United States Patent
Tune et al.

(10) Patent No.: US 7,942,843 B2
(45) Date of Patent: May 17, 2011

(54) IMPLANTATION DEVICE FOR SOFT TISSUE MARKERS AND OTHER IMPLANTS

(75) Inventors: Michal Tune, Doar-Na Hof HaCarmel (IL); David Maier Neustadter, Doar-Na Shimshon (IL); Giora Kornblau, Binyamina (IL); Tal Shchory, Yokneam (IL)

(73) Assignee: Navotek Medical Ltd. (IL)

( * ) Notice: Subject to any disclaimer, the term of this patent is extended or adjusted under 35 U.S.C. 154(b) by 0 days.

(21) Appl. No.: 12/503,907

(22) Filed: Jul. 16, 2009

(65) Prior Publication Data
US 2010/0042041 A1 Feb. 18, 2010

Related U.S. Application Data

(60) Provisional application No. 61/089,571, filed on Aug. 18, 2008.

(51) Int. Cl.
*A61M 31/00* (2006.01)
(52) U.S. Cl. .......................................................... 604/60
(58) Field of Classification Search .................. 600/431, 600/564, 567, 562; 604/57–64, 158, 164.01, 604/197; 623/1.11; 606/191, 192, 167
See application file for complete search history.

(56) References Cited

U.S. PATENT DOCUMENTS

| | | | |
|---|---|---|---|
| 3,777,148 A | 12/1973 | Miraldi | |
| 3,794,840 A | 2/1974 | Scott | |
| 4,096,862 A | 6/1978 | DeLuca | |
| 4,123,654 A | 10/1978 | Reiss et al. | |
| 4,209,700 A | 6/1980 | Stoddart | |
| 4,215,694 A | 8/1980 | Isakov et al. | |
| 4,243,652 A | 1/1981 | Francis | |
| 4,250,392 A | 2/1981 | Leask et al. | |
| 4,645,491 A | 2/1987 | Evans | |
| 4,782,840 A | 11/1988 | Martin, Jr. et al. | |

(Continued)

FOREIGN PATENT DOCUMENTS

EP 0273257 7/1988

(Continued)

OTHER PUBLICATIONS

Communication Relating to the Results of the Partial International Search Dated Jan. 7, 2008 From the International Searching Authority Re.: Application No. PCT/IL2007/000214.

(Continued)

*Primary Examiner* — Christopher D Koharski
(74) *Attorney, Agent, or Firm* — Finnegan, Henderson, Farabow, Garrett & Dunner

(57) ABSTRACT

System and methods disclosed provide a device for inserting an implant with a medical function into body tissue. The device can include a channel passing through the implant, a cannulus with a channel sized to hold the implant, and a pusher with a channel and sized to be situated inside the channel of the cannulus behind the implant, and adapted to push the implant through a distal end of the cannulus into the tissue. The device can also include a restraining element that extends through the channel of the pusher and at least partly through the channel of the implant when they are so situated in the channel of the cannulus, which restrains the implant, but allows the implant to exit the distal end of the cannulus when the implant is pushed with a force small enough so as not to damage the function of the implant in the tissue.

18 Claims, 3 Drawing Sheets

U.S. PATENT DOCUMENTS

| | | | |
|---|---|---|---|
| 4,857,729 A | 8/1989 | Gadeken et al. |
| 4,944,754 A | 7/1990 | Linkow et al. |
| 4,959,547 A | 9/1990 | Carroll et al. |
| 5,114,401 A | 5/1992 | Stuart et al. |
| 5,170,055 A | 12/1992 | Carroll et al. |
| 5,207,223 A | 5/1993 | Adler |
| 5,213,561 A | 5/1993 | Weinstein et al. |
| 5,342,283 A | 8/1994 | Good |
| 5,344,452 A | 9/1994 | Lemperle |
| 5,345,084 A | 9/1994 | Byrd |
| 5,460,592 A | 10/1995 | Langton et al. |
| 5,665,970 A | 9/1997 | Kronenberg et al. |
| 5,694,933 A | 12/1997 | Madden et al. |
| 5,707,332 A | 1/1998 | Weinberger |
| 5,740,808 A | 4/1998 | Panescu et al. |
| 5,813,985 A | 9/1998 | Carroll |
| 5,846,513 A | 12/1998 | Carroll et al. |
| 5,848,967 A | 12/1998 | Cosman |
| 5,933,517 A | 8/1999 | Grangeat et al. |
| 5,938,602 A | 8/1999 | Lloyd |
| 5,961,457 A | 10/1999 | Raylman et al. |
| 5,961,458 A | 10/1999 | Carroll |
| 5,987,350 A | 11/1999 | Thurston |
| 6,016,439 A | 1/2000 | Acker |
| 6,068,623 A | 5/2000 | Zadno-Azizi et al. |
| 6,100,530 A | 8/2000 | Kronenberg et al. |
| 6,188,355 B1 | 2/2001 | Gilboa |
| 6,230,038 B1 | 5/2001 | Von Gutfeld et al. |
| 6,261,243 B1 | 7/2001 | Burney et al. |
| 6,264,599 B1 | 7/2001 | Slater et al. |
| 6,275,724 B1 | 8/2001 | Dickinson et al. |
| 6,332,089 B1 | 12/2001 | Acker et al. |
| 6,363,940 B1 | 4/2002 | Krag |
| 6,371,904 B1 | 4/2002 | Sirimanne |
| 6,380,732 B1 | 4/2002 | Gilboa |
| 6,402,677 B1 | 6/2002 | Jacobs |
| 6,419,621 B1 | 7/2002 | Sioshansi et al. |
| 6,427,314 B1 | 8/2002 | Acker |
| 6,436,026 B1 | 8/2002 | Sioshansi et al. |
| 6,491,619 B1 | 12/2002 | Trauthen et al. |
| 6,496,717 B2 | 12/2002 | Cox et al. |
| 6,510,336 B1 | 1/2003 | Daghighian et al. |
| 6,558,612 B1 | 5/2003 | Hubbard |
| 6,580,938 B1 | 6/2003 | Acker |
| 6,593,884 B1 | 7/2003 | Gilboa et al. |
| 6,603,124 B2 | 8/2003 | Maublant |
| 6,618,612 B1 | 9/2003 | Acker et al. |
| 6,675,810 B2 | 1/2004 | Krag |
| 6,690,963 B2 | 2/2004 | Ben-Haim et al. |
| 6,698,433 B2 | 3/2004 | Krag |
| 6,711,429 B1 | 3/2004 | Gilboa et al. |
| 6,749,555 B1 | 6/2004 | Winkler et al. |
| 6,751,492 B2 | 6/2004 | Ben-Haim |
| 6,788,967 B2 | 9/2004 | Ben-Haim et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,847,838 B1 | 1/2005 | Macey et al. |
| 6,889,833 B2 | 5/2005 | Seiler et al. |
| 6,918,919 B2 | 7/2005 | Krag |
| 6,920,347 B2 | 7/2005 | Simon et al. |
| 6,977,504 B2 | 12/2005 | Wright et al. |
| 7,047,063 B2 | 5/2006 | Burbank et al. |
| 7,066,924 B1 | 6/2006 | Garibaldi et al. |
| 7,247,160 B2 | 7/2007 | Seiler et al. |
| 7,289,839 B2 | 10/2007 | Dimmer et al. |
| 7,407,054 B2 | 8/2008 | Seiler et al. |
| 2001/0005930 A1 | 7/2001 | Coniglione |
| 2002/0058853 A1 | 5/2002 | Kaplan |
| 2002/0077533 A1 | 6/2002 | Bieger et al. |
| 2002/0087078 A1 | 7/2002 | Cox et al. |
| 2002/0193685 A1 | 12/2002 | Mate et al. |
| 2003/0040737 A1 | 2/2003 | Merril et al. |
| 2003/0088140 A1 | 5/2003 | Terwilliger et al. |
| 2004/0034297 A1 | 2/2004 | Darrow et al. |
| 2004/0037394 A1 | 2/2004 | Kuroda et al. |
| 2004/0068157 A1 | 4/2004 | Gellman et al. |
| 2004/0073107 A1 | 4/2004 | Sioshansi et al. |
| 2004/0116767 A1 | 6/2004 | Lebovic et al. |
| 2004/0204672 A1* | 10/2004 | Palasis et al. ............ 604/57 |
| 2004/0236213 A1 | 11/2004 | Jones et al. |
| 2005/0010099 A1 | 1/2005 | Raabe et al. |
| 2005/0027196 A1 | 2/2005 | Fitzgerald |
| 2005/0054910 A1 | 3/2005 | Tremblay et al. |
| 2005/0055174 A1 | 3/2005 | David et al. |
| 2005/0085717 A1 | 4/2005 | Shahidi |
| 2005/0197564 A1 | 9/2005 | Dempsey |
| 2005/0245814 A1 | 11/2005 | Anderson et al. |
| 2005/0261570 A1 | 11/2005 | Mate et al. |
| 2007/0055090 A1 | 3/2007 | Neustadter et al. |
| 2007/0055144 A1 | 3/2007 | Neustadter et al. |
| 2007/0123817 A1* | 5/2007 | Khosravi et al. ............ 604/57 |
| 2007/0205373 A1 | 9/2007 | Kornblau et al. |
| 2007/0265491 A1 | 11/2007 | Krag et al. |
| 2008/0262473 A1 | 10/2008 | Kornblau et al. |

FOREIGN PATENT DOCUMENTS

| | | |
|---|---|---|
| EP | 0466681 | 1/1992 |
| EP | 0531081 | 3/1993 |
| EP | 0993843 | 4/2000 |
| EP | 1060764 | 12/2000 |
| FR | 1561351 | 3/1969 |
| GB | 2330263 | 4/1999 |
| JP | 01-288250 | 11/1989 |
| WO | WO 97/29699 | 8/1997 |
| WO | WO 97/29700 | 8/1997 |
| WO | WO 99/21615 | 5/1999 |
| WO | WO 99/35966 | 7/1999 |
| WO | WO 00/24332 | 5/2000 |
| WO | WO 00/57923 | 10/2000 |
| WO | WO 00/71204 | 11/2000 |
| WO | WO 01/30447 | 5/2001 |
| WO | WO 01/54765 | 8/2001 |
| WO | WO 01/87409 | 11/2001 |
| WO | WO 02/16965 | 2/2002 |
| WO | WO 02/39142 | 5/2002 |
| WO | WO 02/39917 | 5/2002 |
| WO | WO 02/39918 | 5/2002 |
| WO | WO 02/078785 | 10/2002 |
| WO | WO 03/011161 | 2/2003 |
| WO | WO 03/032837 | 4/2003 |
| WO | WO 2004/026111 | 4/2004 |
| WO | WO 2006/004542 | 1/2006 |
| WO | WO 2006/016368 | 2/2006 |
| WO | WO 2006/043276 | 4/2006 |
| WO | WO 2007/017846 | 2/2007 |
| WO | WO 2007/017847 | 2/2007 |
| WO | WO 2007/094001 | 8/2007 |
| WO | WO 2007/094002 | 8/2007 |

OTHER PUBLICATIONS

International Preliminary Report on Patentability Dated May 9, 2007 From the International Preliminary Examining Authority Re.: Application No. PCT/IL05/01101.

International Preliminary Report on Patentability Dated Apr. 12, 2007 From the International Bureau of WIPO Re.: Application No. PCT/IL2005/000871.

International Preliminary Report on Patentability Dated Feb. 21, 2008 From the International Preliminary Examining Authority Re.: Application No. PCT/IB2006/052770.

International Preliminary Report on Patentability Dated Nov. 27, 2007 From the International Preliminary Examining Authority Re.: Application No. PCT/IB2006/052771.

International Preliminary Report on Patentability Dated Aug. 28, 2008 From the International Bureau of WIPO Re.: Application No. PCT/IL2007/000215.

International Preliminary Report on Patentability Dated Aug. 26, 2008 From the International Preliminary Examining Authority Re.: Application No. PCT/IL2007/000214.

International Search Report Dated Jan. 3, 2007 From the International Searching Authority Re.: Application No. PCT/IB2006/052771.

International Search Report Dated Mar. 6, 2007 From the International Searching Authority Re.: Application No. PCT/IL05/00871.

International Search Report Dated Jan. 7, 2008 From the International Searching Authority Re.: Application No. PCT/IL2007/000215.
International Search Report Dated Sep. 10, 2007 From the International Searching Authority Re.: Application No. PCT/IB2006/052770.
International Search Report Dated Feb. 29, 2008 From the international Searching Authority Re.: Application No. PCT/IL2007/000214.
International Search Report Dated May 30, 2006 From the International Searching Authority Re.: Application No. PCT/IL05/01101.
Official Action Dated Jun. 24, 2009 From the US Patent and Trademark Office Re.: U.S. Appl. No. 10/599,963.
Written Opinion Dated Jan. 3, 2007 From the International Searching Authority Re.: Application No. PCT/IB2006/052771.
Written Opinion Dated Mar. 6, 2007 From the International Searching Authority Re.: Application No. PCT/IL05/00871.
Written Opinion Dated Jan. 7, 2008 From the International Searching Authority Re.: Application No. PCT/IL2007/000215.
Written Opinion Dated Sep. 10, 2007 From the International Searching Authority Re.: Application No. PCT/IB2006/052770.
Written Opinion Dated Feb. 29, 2008 From the International Searching Authority Re.: Application No. PCT/IL2007/000214.
Calipso "Calypso® 4D Localization System-GPS for the Body", Calypso® Medical: Products & Technology—The Problem, Downloaded From <http://calypsomedical.com/products/> on Dec. 12, 2002.
Kirsch et al. "Real Time Tracking of Tumor Positions for Precision Irradiation", CAR'98, Computer Assisted Radiology and Surgery, Proceedings of the International Congress and Exhibition, Proceedings of the International Symposium on Computer Assisted Radiology and Surgery, p. 262-264, 1998.
Lengyel et al. "Three-Dimensional Reconstruction and Volume Rendering of Intravascular Ultrasound Slices Imaged on a Curved Arterial Path", Computer Vision, Virtual Reality and Robotics in Medicine, Lecture Notes in Computer Science, 905: 399-405, 1995. Abstract.
Amendment in Response to Restriction Requirement Dated Nov. 16, 2009 From the US Patent and Trademark Office Re.: U.S. Appl. No. 11/635,441.
International Preliminary Report on Patentability Dated Dec. 12, 2006 From the International Preliminary Examining Authority Re.: Application No. PCT/IL2005/01101.
Preliminary Amendment Dated Sep. 26, 2008 From the US Patent and Trademark Office Re.: U.S. Appl. No. 11/635,441. not by us!
Response Dated Jan. 14, 2010 to Examination Report of Oct. 27, 2009 From the Instituto Mexicano de la Propriedad Industrial Re.: Application No. MX/a/2007/001783.
Response Dated Feb. 25, 2010 to Official Action of Oct. 29, 2009 From the US Patent and Trademark Office Re.: U.S. Appl. No. 11/463,659.
Response Dated Jan. 31, 2010 to Office Action of Aug. 7, 2009 From the State Intellectual Property Office of the People's Republic of China Re.: Application No. 200580034274.1.
Second Preliminary Amendment Dated Jul. 20, 2007 Re.: U.S. Appl. No. 11/635,441.
Translation of Office Action Dated Jan. 22, 2010 From the State Intellectual Property Office of the People's Republic of China Re.: Application No. 200680037432.3.

* cited by examiner

IMPLANTATION DEVICE FOR SOFT TISSUE MARKERS AND OTHER IMPLANTS

RELATED APPLICATIONS

This applications claims benefit under 35 U.S.C. §119(e) of U.S. Provisional Patent Application No. 61/089,571, filed on Aug. 18, 2008.

This application is also related to PCT Patent Application No. PCT/IL2007/000214, filed on Feb. 15, 2007, which is a Continuation-In-Part of PCT Patent Application No. PCT/IB2006/052771, filed on Aug. 10, 2006 and PCT Patent Application No. PCT/IB2006/052770, filed on Aug. 10, 2006, and which claims priority from U.S. Provisional Patent Application No. 60/773,931, filed on Feb. 16, 2006, U.S. Provisional Patent Application No. 60/773,930, filed on Feb. 16, 2006 and U.S. Provisional Patent Application No. 60/804,178, filed on Jun. 8, 2006. It is also related to PCT Patent Application No. PCT/IL2005/000871, filed on Aug. 11, 2005, PCT Patent Application No. PCT/IL2005/001101, filed on Oct. 19, 2005, U.S. Provisional Patent Application No. 60/600,725, filed on Aug. 12, 2004, U.S. Provisional Patent Application No. 60/619,792, filed on Oct. 19, 2004, U.S. Provisional Patent Application No. 60/619,897, filed on Oct. 19, 2004, U.S. Provisional Patent Application No. 60/619,898, filed on Oct. 19, 2004, U.S. patent application Ser. No. 11/463,664, filed on Aug. 10, 2006 and U.S. patent application Ser. No. 11/463,659, filed on Aug. 10, 2006.

The disclosure of each of these applications is incorporated herein by reference.

FIELD AND BACKGROUND OF THE INVENTION

The present invention, in some embodiments thereof, relates to a device for inserting medical implants into tissue and, more particularly, but not exclusively, to a device for inserting soft tissue markers.

Soft tissue implants include markers that are used to mark the site of a biopsy or another surgical procedure or medical treatment, for defining the location of the procedure or treatment before it is performed, or for marking a location where the procedure or treatment was performed, for future follow up medical procedures. Soft tissue implants also include therapeutic implants, for example for brachytherapy. The implant, whether it is used as a marker or for another purpose, is often inserted using a device that comprises a hollow needle or other cannulus structure, with a sharpened end for penetrating to a desired location in the tissue, and with the implant loaded into a channel inside the cannulus. The device may or may not be part of an instrument that is also used for the surgery or biopsy. The device sometimes has an obstruction that prevents the implant from accidentally leaving the device before the operator of the device is ready to implant it, so that it can be positioned precisely, and means for removing or circumventing the obstruction, and inserting the implant into the tissue, when it is properly positioned. An example of such a device with an obstruction is shown in FIGS. 1A-1C, and described below.

U.S. Pat. No. 6,261,243, to Burney et al, describes a cannulus for inserting a soft tissue marker, with an opening in the side of the cannulus. A sliding cover prevents the marker from leaving the cannulus until the cannulus is properly positioned.

US Patent Application Publication No. 2004/0236213, to Jones et al, describes a device with a cannulus holding a soft tissue marker, and a plug made of wax covering an opening at the end. The marker is pushed from behind by a stylet, which pushes hard enough to push the plug out of the cannulus, allowing the marker to emerge.

A similar device is described in U.S. Pat. No. 7,247,160 to Seiler et al, but instead of pushing the marker and the plug forward out of the cannulus, the cannulus is pulled back, while using the stylet to hold the marker and plug in place. This breaks the plug free from the cannulus, leaving the marker and the plug is place in the tissue, and may allow more accurate placement of the marker than if the cannulus is held in place and the marker and plug are pushed forward.

U.S. Pat. No. 7,047,063, to Burbank, describes a device for inserting a marker into soft tissue, in which the marker is placed in a cannulus that has a closed petaled end. When the marker is pushed from behind by a stylet, the marker pushes open the petals at the end of the cannulus, allowing the marker to emerge.

U.S. Pat. No. 6,402,677, to Jacobs, describes a device for inserting brachytherapy seeds into soft tissue. The seeds are placed in a cannulus, which has an end that is partly blocked by an obstruction. A stylet pushes the brachytherapy seeds with enough force to go past the obstruction, and leave the cannulus.

Soft tissue markers, as well as brachytherapy implants, are sometimes formed in the shape of a helical coil. Such implants are described, for example, in U.S. Pat. Nos. 6,261,243 and 7,047,063, cited above, and in US Patent Application Publication No. 2004/0073107 to Sioshansi, as well as International Publication No. WO00/24332 to Cortese, and U.S. Pat. No. 6,371,904 to Sirimanne.

SUMMARY OF THE INVENTION

An aspect of an embodiment of the invention concerns a device for inserting an easily deformed medical implant, with a restraining element that keeps the implant from leaving the device accidentally, but allows the implant to leave the device when relatively little force is exerted on it, so it will not be damaged.

There is thus provided, in accordance with an exemplary embodiment of the invention, a device for inserting into body tissue an implant with a medical function, with a channel passing at least partly through the implant, the device comprising:

a) a cannulus with a distal end, and with a channel sized to hold the implant;

b) a pusher with a channel passing through it, the pusher sized to be situated inside the channel of the cannulus behind the implant, and adapted to push the implant through the distal end of the cannulus into the tissue;

c) a restraining element that extends through the channel of the pusher and at least partly through the channel of the implant when they are so situated in the channel of the cannulus, which restrains the implant from accidentally exiting the cannulus, but allows the implant to exit the distal end of the cannulus when it is pushed with a force small enough so as not to damage the function of the implant in the tissue.

Optionally, the implant is a soft tissue marker.

Optionally, the implant comprises a helical coil.

Optionally, the channel of the implant extends all the way through the implant.

Optionally, the restraining element has a distal end that extends past the distal end of the implant when the implant and pusher are so situated, hut not past the distal end of the cannulus, and the distal end of the restraining element restrains the implant from sliding off the restraining element.

Optionally, the distal end of the restraining element bends to one side, but is flexible enough to straighten sufficiently so that the implant can slide off it, when the implant is pushed with said force.

In an embodiment of the invention, the restraining element comprises a wire.

Optionally, a distal end of the restraining element is enlarged, but is configured so that the implant can slide off it, when the implant is pushed with said force.

Optionally, the restraining element restrains the implant by friction against a surface of the channel of the implant.

In an embodiment of the invention, the function of the implant comprises folding on itself to define a volume with a smallest dimension greater than the diameter of the channel of the cannulus, when the implant is inserted into the tissue.

Optionally, the restraining element is least indirectly coupled to the cannulus, such that the restraining element does not move along the cannulus when the pusher pushes the implant through the distal end of the cannulus.

Optionally, the device also includes a handle, wherein the cannulus and the restraining element are anchored in the handle at their proximal ends.

Optionally, the device also includes a handle adapted to be held by an operator with one hand when using the device to insert the implant in the tissue.

There is further provided, in accordance with an exemplary embodiment of the invention, a method of inserting a medical implant into tissue, comprising:

a) loading the implant into a channel of a cannulus, with a restraining element extending at least part way through a channel in the implant, restraining the implant from leaving the cannulus accidentally before insertion into the tissue;

b) inserting a distal end of the cannulus into the tissue; and c) pushing the implant out of the distal end of the cannulus, with a large enough force so that the implant moves past the restraining element, but with a small enough force so that the implant is not damaged and functions properly in the tissue.

Optionally, proper functioning of the implant in the tissue comprises the implant folding on itself when inserted into the tissue, to define a volume with smallest dimension greater than the diameter of the cannulus.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1A:
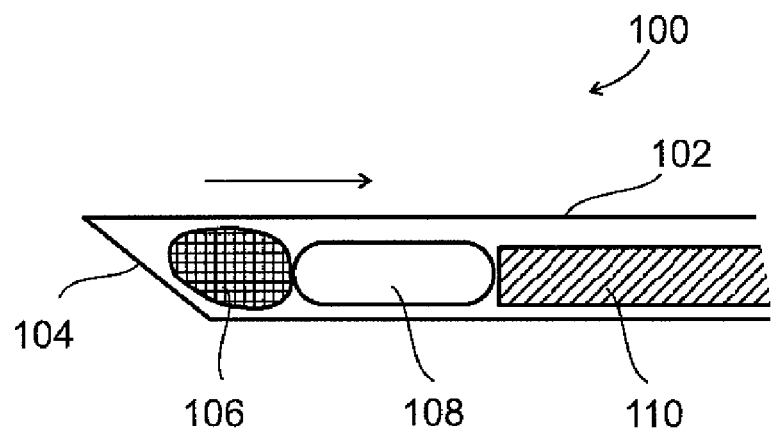
FIGS. 1A-1C schematically show a time sequence of inserting a marker or other implant in soft tissue, according to the prior art.

The present invention, in some embodiments thereof, relates to a device for inserting medical implants into tissue and, more particularly, but not exclusively, to a device for inserting soft tissue markers.

An aspect of an embodiment of the invention concerns a device with a cannulus, for inserting a medical implant, for example a soft tissue marker, into soft tissue, and with a restraining element that restrains the implant from leaving the device accidentally, but allows the implant to be pushed gently out of the device into the tissue. The restraining element extends at least part way through a channel in the implant, and through a channel in a pusher, situated behind the implant, that pushes the implant out of the cannulus, and the restraining element is optionally directly or indirectly anchored to the cannulus. The pushing needed to overcome the restraint of the restraining element is gentle enough so that the implant is not damaged, and can still perform its function in the tissue. For example, the implant is a soft tissue marker that is designed to fold on itself, as a result of the force it encounters when it is inserted into the tissue, defining a volume that is greater in diameter than the channel of the cannulus, making the marker more stable within the tissue and more visible in medical imaging. Such markers are described in related PCT Patent Application No. PCT/IL2007/000214, cited above. Particularly in a case where the implant is easily deformable, it may be advantageous not to push on it too hard before it is inserted into the tissue.

Optionally, the restraining element is a wire that extends through the channel in the implant to its distal end, and has a bend at the end that restrains the implant from sliding off it and exiting the cannulus, but the wire is flexible enough, and the channel in the implant is wide enough, so that the implant can be pushed past the bent end of the wire with relatively little force. Optionally, whether or not the restraining element extends to the distal end of the implant, it uses friction with the channel through the implant, in order to restrain the implant from moving past it.

It should be noted that prior methods of restraining an implant before it is ready to be implanted, such as those described above, are generally not well suited to an implant that is designed to fold on itself and define an increased volume, when it leaves the cannulus. When the implant has to push against a wax plug, or a petalled end, for example, in order to exit the cannulus, a relatively large force is generally applied to the implant. A large pushing force is generally needed, because the plug or other barrier is designed not to fail accidentally. If the implant is easily deformable, as it may tend to be if it is designed to fold on itself when it exits the cannulus, then the large pushing force may deform the implant before it leaves the cannulus. Such deformation may actually prevent the implant from leaving the cannulus, and if it does leave the cannulus, it may not fold properly after it leaves the cannulus. Such an implant may also not fold on itself if the cannulus is pulled away from the implant, rather than pushing the implant out of the cannulus. And having such an implant exit the cannulus from an opening on the side may also not to be suitable, since it may not fold properly.

A potential advantage of using a restraining element that is anchored to the cannulus, and passes through a channel in the implant and in the pushing element, is that the restraining element cannot easily break off or otherwise fail, but only a small force may be needed to overcome the restraining element when the implant is pushed out of the cannulus. This behavior is in contrast to that of a wax plug, for example, which may easily break off prematurely, if it requires only a small force to push it off the cannulus.

Figure 1B:
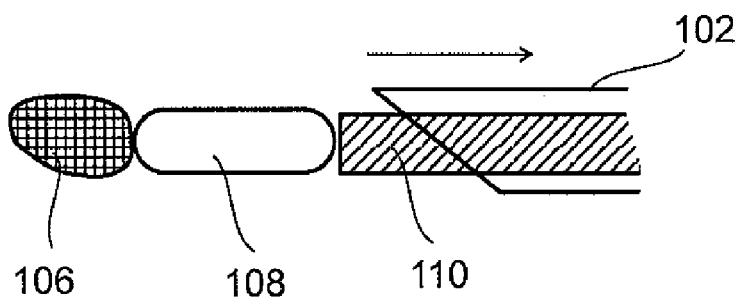
Figure 1C:
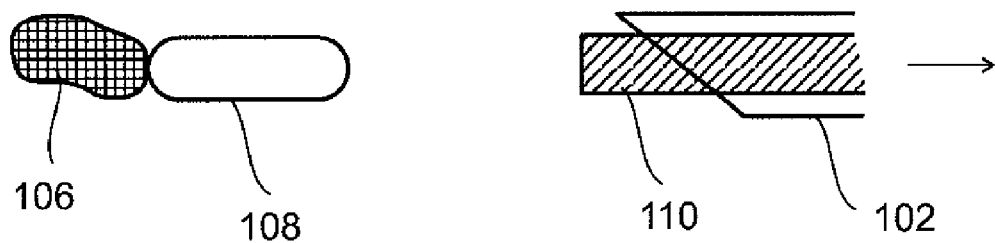

For purposes of better understanding some embodiments of the present invention, as illustrated in FIGS. 2A-5 of the drawings, reference is first made to the construction and operation of a conventional (i.e., prior art) device 100 for inserting a soft tissue implant, as illustrated in FIGS. 1A-1C. As seen in FIG. 1A, device 100 comprises a cannulus 102, with a distal end 104 that is sharpened for penetrating into the tissue, and is open. The opening of end 104 is sealed by a plug 106, made of bone wax, for example. An implant 108, such as a marker or a brachytherapy seed, is loaded behind plug 106 in cannulus 102, with a stylet 110 extending from the proximal end of cannulus 102 up to implant 108. Plug 106 prevents implant 108 from leaving cannulus 102 accidentally, before the cannulus is in position for inserting the implant. Once the cannulus is properly positioned, it is pulled back, as shown in FIG. 1B, while stylet 110 is held in place, leaving plug 106 and implant 108 in place. Cannulus 102 is pulled back with sufficient force that it becomes detached from plug 106, allowing plug 106 and implant 108 to leave cannulus 102 through distal end 104. This requires a relatively large force, because plug 106 is attached firmly to cannulus 102 initially, in order to ensure that plug 106 does not come off prematurely. Cannulus 102, with stylet 110, is then removed from the tissue, leaving plug 106 and implant 108 in the tissue.

In other prior art devices, cannulus 102 is held in place, while stylet 110 pushes implant 108 and plug 106 forward, out of cannulus 102 through distal end 104. This may require even more force than pulling the cannulus back, since the marker and plug must overcome the pressure of the tissue, in addition to the force needed to detach the plug from the cannulus. The end result is the same, with the marker and plug remaining in the tissue.

As noted above, the device and method shown in FIGS. 1A-1C may not be suitable for inserting an implant of a type that is designed to fold on itself when it is inserted into the tissue. The plug, which is left in the tissue, may be more difficult to sterilize than the marker, and it may irritate the tissue, even if it is eventually absorbed.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 2A:
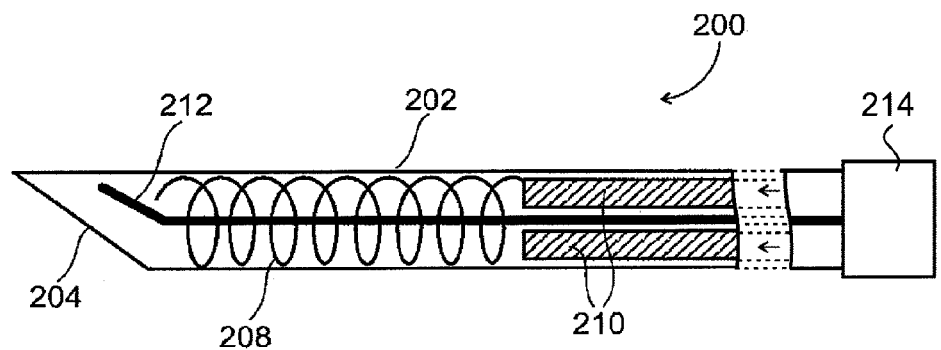
FIGS. 2A-2C schematically show a time sequence of inserting a marker in soft tissue, according to an exemplary embodiment of the invention.

Referring now to the drawings, FIG. 2A shows a device 200 for inserting an implant into soft tissue, according to an exemplary embodiment of the invention. Device 200 comprises a cannulus 202 with a sharpened open end 204, similar to cannulus 102. There is no plug blocking the open end of cannulus 202. An implant 208, for example a helical marker, is placed near the distal end of cannulus 202, with a pusher 210 behind it. Both implant 208 and pusher 210 have channels running through them. A restraining element 212 extends through the channels of pusher 210 and implant 208, optionally extending past the distal end of implant 208. In the configuration shown in FIG. 2A, restraining element 212 is a wire, bent at its distal end, and this bend keeps implant 208 from sliding off restraining element 212, and out distal end 204, prematurely. Optionally, the distal end of restraining element 212 touches the wall of cannulus 202, leaving no space for implant 208 to slide past it. Even if the distal end of restraining element 212 does not extend all the way to the wall, it may restrain implant 208 from moving past it by getting in its way, or by friction.

Figure 2B:
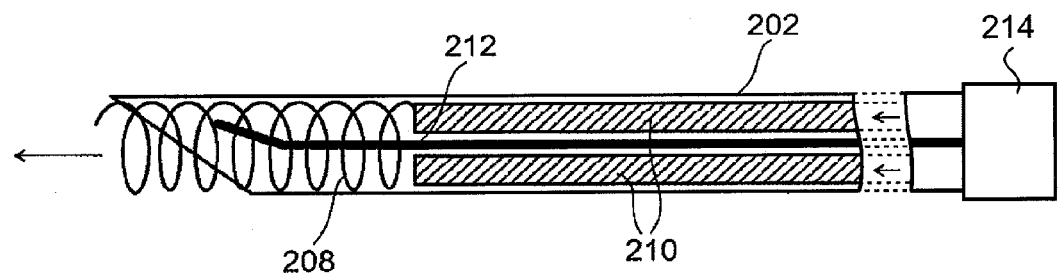

When device 200 has been positioned in the soft tissue, at a location where implant 208 is to be inserted, then pusher 210 is pushed forward against implant 208, as shown in FIG. 2B, while cannulus 202 and restraining element 212 do not move forward. Optionally, restraining element 212 is anchored to cannulus 202, for example at their proximal end at a handle 214 that is used to hold device 200, or at least indirectly coupled to cannulus 202, such that restraining element 212 does not move along cannulus 202 when pusher 210 pushes implant 208 along cannulus 202.

When pusher 210 is pushed forward against implant 208, implant 208 moves forward, over restraining element 212. Relatively little force is needed to make implant 208 do this, since it takes relatively little force to slightly decrease the bend in restraining element 212, so implant 208 can fit over it. Although implant 208 may compress somewhat even from this relatively small force, it does not deform to such an extent, when it is still inside cannulus 202, that it will be unable to fold on itself when it leaves cannulus 202.

Optionally, the force needed to push the implant past the restraining element, in device 200 or any other embodiment of the invention, is greater than the weight of the implant, or greater than 2 times or 5 times or 10 times or 20 times or 50 times or 100 times the weight of the implant. The weight of the implant is, for example, 0.5 milligrams, or 1 milligram, or 2 milligrams, or 5 milligrams, 10 milligrams, or a greater or lesser or intermediate weight. Optionally, the force needed to overcome the restraining element is less than a force needed to deform the implant irreversibly. Optionally the force needed to overcome the restraining element, plus the greatest force that would normally be needed to overcome any friction of the implant with the cannulus, is less than a force needed to deform the implant irreversibly, or at least less than a force needed to deform the implant irreversibly to such an extent that it will not fold properly when it leaves the cannulus.

Figure 2C:
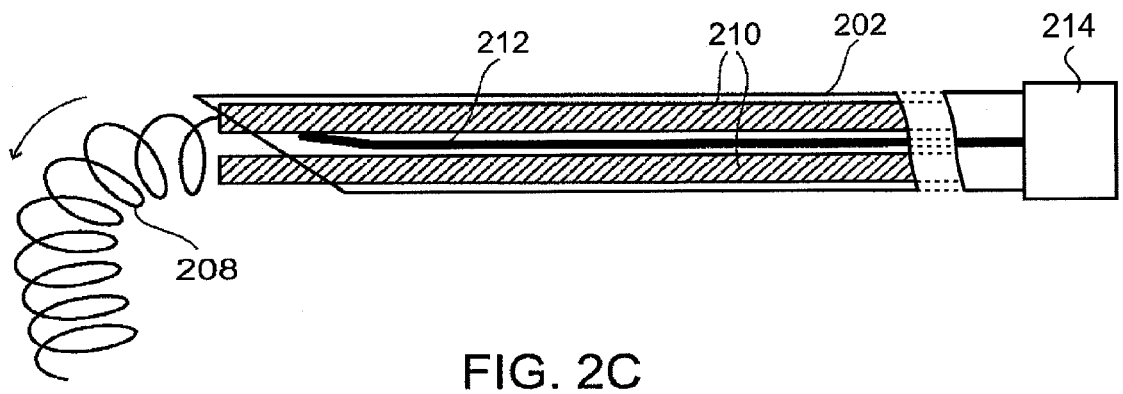

FIG. 2C shows device 200 when implant 208 has been completely pushed out of cannulus 202. Due to the pressure of the tissue, implant 208 has folded on itself, as it is designed to do, forming a generally irregular shape defining a volume that is wider, in its smallest dimension, than the inside diameter of the cannulus. Restraining element 212 is now completely inside the channel of pusher 210, but is flexible enough so that it can unbend enough to fit inside the channel of pusher 210, without the need to exert very much force on it. Device 200 can then be withdrawn from the tissue, leaving implant 208 in place in the tissue.

Restraining element 212 is optionally stiff enough so that its distal bend will not unbend under the weight of implant 208 during handling of the device, allowing implant 208 to fall out if device 200 is held with distal end 204 facing downward. But restraining element is flexible enough so that it will unbend in response to a force on implant 208 that will not prevent implant 208 from functioning properly when it is inserted in the tissue, folding on itself to form an increased volume.

Figure 3:
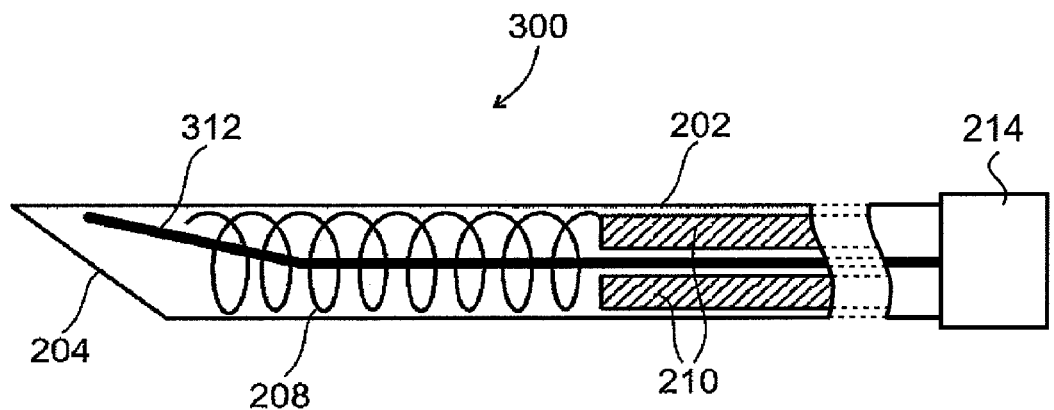
FIG. 3 schematically shows a device for inserting a marker into soft tissue, according to another exemplary embodiment of the invention.
Figure 4:
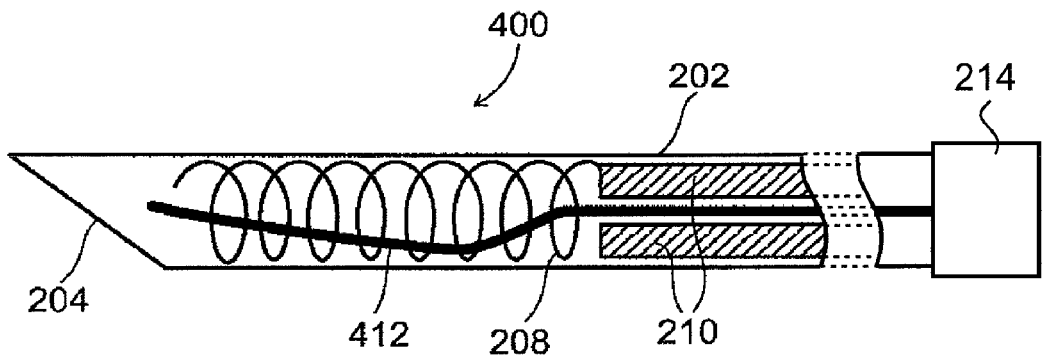
FIG. 4 schematically shows a device for inserting a marker into soft tissue, according to another exemplary embodiment of the invention.

FIGS. 3 and 4 show implant devices 300 and 400 with alternative designs for the restraining element. In FIG. 3, a restraining element 312 has a gentle curvature, optionally over its whole length, or at least over a portion that is outside the channel of pusher 210. The curvature is sufficiently great that, over the length of restraining element 312 that is initially outside the channel of pusher 210, the distal end of restraining element 312 reaches the wall of cannulus 202, or sufficiently close to the wall of cannulus 202 that implant 208 cannot easily slide off restraining element 312. For example, the distal end of restraining element 312 extends radially past the surface of the channel through implant 208, so that element 312 blocks implant 208 from sliding off it, at least when there is sufficiently little force pushing it. As pusher 210 is pushed forward, to the left in FIG. 3, with sufficient force, the portion of restraining element 312 outside pusher 210 gets shorter. With the same curvature, and with the rest of the restraining element constrained to follow the channel of pusher 210, the distal end of restraining element 312 moves closer to the center of the channel of cannulus 202. This would tend to occur even without any force from implant 208, although implant 208 may exert an additional force on restraining element 312, tending to make it straighter. In any case, with restraining element 312 confined closer to the center of the channel of cannulus 202, implant 208 can move past restraining element 312 and out of end 204 of cannulus 202, into the tissue.

In the embodiment shown in FIG. 4, a restraining element 412 has a bend downward, near the point where it emerges from the channel of pushing element 210, and then curves upward for the rest of its length. Although the geometry of this distal portion of restraining element 412 does not prevent implant 208 from sliding off it, the force of restraining element 412 pushing implant 208 against the wall of cannulus 202 at the bottom of FIG. 4 tends to prevent implant 208 from moving, due to friction of implant 208 with the wall of cannulus 202. The force of friction is, for example, a coefficient of friction times the force with which element 412 pushes implant 208 against the wall. Optionally, this force of friction is more than great enough to prevent implant 208 from sliding along restraining element 412 under its own weight, but is small enough so that implant 208 can be pushed off restraining element 412, and out of cannulus 202 into the tissue, with a relatively small force exerted by pusher 210. In particular, this force is small enough so that implant 208 will not deform so much that it cannot function properly when it is inserted into the tissue, as explained previously.

It should be noted that, for restraining elements 212 and 312 as well, the end of the restraining element need not extend past the end of implant 208, but the end of the restraining element can restrain implant 208 from moving by friction between the restraining element and the inner surface of implant 208, and/or by pushing implant 208 against the inner surface of cannulus 202, and using friction between implant 208 and cannulus 202 to restrain implant 208 from sliding out of cannulus 202.

Figure 5:
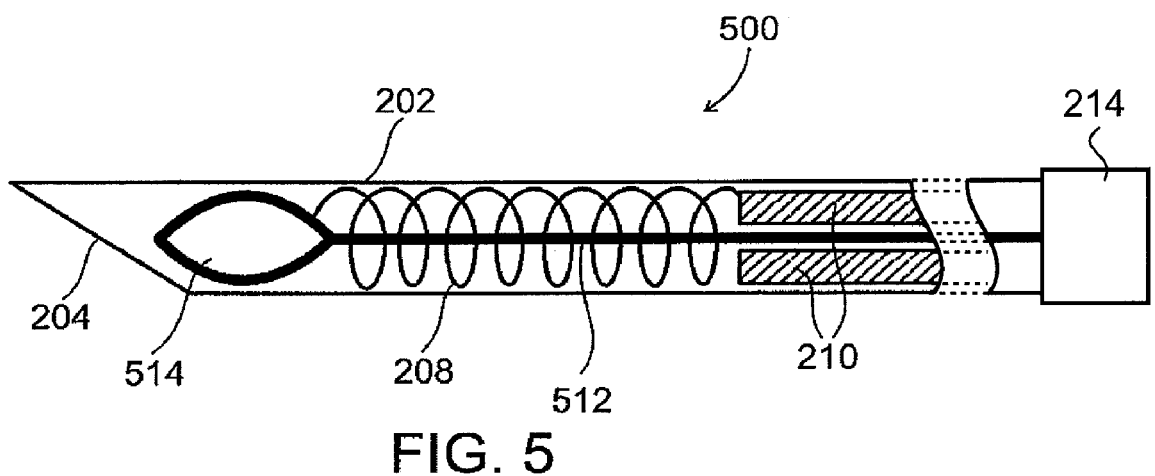
FIG. 5 schematically shows a device for inserting a marker into soft tissue, according to another exemplary embodiment of the invention.

In device 500 shown in FIG. 5, a restraining element 512 has an enlarged end 514, optionally compressible, which prevents implant 208 from sliding off restraining element 512 before implanting, for example because of friction, or because enlarged end 514 has too great a diameter for implant 208 to slide past. When cannulus 202 is positioned for inserting implant 208 into the tissue, pusher 210 pushes implant 208 with enough force so that is slides past enlarged end 514, optionally by compressing enlarged end 514. The required force to push implant 208 past enlarged end 514 is small enough so that implant 208 is not damaged, but still functions properly in the tissue.

Enlarged end 514 could have a number of different possible configurations, and the shape shown in FIG. 5 is only exemplary. Optionally, enlarged end 514 comprises a flexible or compressible structure which can be compressed radially toward the axis of cannulus 202, allowing implant 208 to go past restraining element 512, when pusher 210 pushes implant 208 forward. For example, enlarged end 514 optionally comprises two or more rod-like extensions extending radially or obliquely away from the axis of element 512 in different directions. Additionally or alternatively, enlarged end 514 comprises a set of two or more leaf springs, or similar structures which can be pressed toward the axis by implant 208. Additionally or alternatively, enlarged end 514 comprises a balloon, optionally a compressible balloon. Additionally or alternatively, enlarged end 514 comprises a compressible sponge-like material. Additionally or alternatively, whether enlarged end 514 is compressible or relatively rigid, enlarged end 514 just fits within implant 208 as implant 208 slides past it, such that the force of friction prevents implant 208 from sliding off enlarged end 514 unless implant 208 is pushed with sufficient force by pusher 210.

Showing implant 208 in the form of a coil is FIGS. 2A-5 is merely exemplary, and implant 208 need not be in the form of a coil, but can be of any configuration with a channel into which the restraining element extends. For example, the implant may comprise a cylindrical shell, optionally with perforations in the shell, or with accordion-like folds in the shell. Optionally the perforations comprise most or almost all of the area of the shell.

Optionally the channel through the implant does not extend through the whole length of the implant, but is blocked at the distal end, or at another location, and the restraining element does not extend distally past the location where the channel is blocked.

Optionally, the channel through the implant is not completely surrounded by the implant azimuthally, but is open in one direction, with the channel comprising an axially oriented slot or indentation in the implant. In this case, the geometry of the implant, the restraining element and the cannulus prevents the restraining element from slipping out of the channel of the implant, when the implant is still in the cannulus. In fact, a helical implant, with the end turns of the helix open, is a special case of such a geometry, with the "slot" being the spiral space between adjacent turns of the helix. Alternatively, for example if the implant is a cylindrical shell, or a helical coil with closed end turns, the implant topologically surrounds the restraining element, which cannot slip out of the channel of the implant except by moving forward off the distal end of the restraining element.

In many of the embodiments of the invention shown in FIGS. 2A-5, and described above, the implant exerts a radially inward force on the restraining element as it is moving past it, on the way out of the cannulus, and conversely the restraining element exerts a radially outward force on the implant. This has the potential advantage that it may help to maintain the shape of the implant, and prevent it from deforming, when it is being pushed out of the cannulus. Possibly this outward radial force on the implant could allow the implant to be pushed with greater force axially, without deforming it to an extent that it wouldn't fold properly when it leaves the cannulus.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for inserting into body tissue an implant with a medical function, with a channel passing at least partly through the implant, the device comprising:
    a cannulus with a distal end, and with a channel sized to hold the implant;
    a pusher with a channel passing through the pusher, the pusher sized to be situated inside the channel of the cannulus behind the implant, and adapted to push the implant through the distal end of the cannulus into the tissue; and
    a restraining element that extends through the channel of the pusher and at least partly through the channel of the implant when they are so situated in the channel of the cannulus, which is configured to couple with the implant to restrain the implant within the cannulus, and is further configured to couple with the implant to allow the implant to exit the distal end of the cannulus when the implant is pushed with a force small enough so as not to damage the function of the implant in the tissue;
    wherein the channel of the implant extends all the way through the implant,
    wherein the restraining element has a distal end that extends past the distal end of the implant when the implant and pusher are so situated, but not past the distal end of the cannulus, and the distal end of the restraining element restrains the implant from sliding off the restraining element, and
    wherein the distal and of the restraining element bends to one side, but is flexible enough to straighten sufficiently so that the implant can slide off the distal end of the restraining element, when the implant is pushed with said force.

2. A device according to claim 1, wherein the implant is a soft tissue marker.

3. A device according to claim 1, wherein the implant comprises a helical coil.

4. A device according to claim 1, wherein the restraining element comprises a wire.

5. A device according to claim 1, wherein the restraining element restrains the implant by friction against a surface of the channel of the implant.

6. A device according to claim 1, wherein the function of the implant comprises folding on itself to define a volume with a smallest dimension greater than the diameter of the channel of the cannulus, when the implant is inserted into the tissue.

7. A device according to claim 1, wherein the restraining element is at least indirectly coupled to the cannulus, such that the restraining element does not move along the cannulus when the pusher pushes the implant through the distal end of the cannulus.

8. A device according to claim 7, also including a handle, wherein the cannulas and the restraining element are anchored in the handle at their proximal ends.

9. A device according to claim 1, also including a handle adapted to be held by an operator with one hand when using the device to insert the implant in the tissue.

10. A device for inserting into body tissue an implant with a medical function, with a channel passing at least partly through the implant, the device comprising:
    a cannulus with a distal end, and with a channel sized to hold the implant;
    a pusher with a channel passing through the pusher, the pusher sized to be situated inside the channel of the cannulus behind the implant, and adapted to push the implant through the distal end of the cannulus into the tissue; and
    a restraining element that extends through the channel of the pusher and at least partly through the channel of the implant when they are so situated in the channel of the cannulus, which is configured to couple with the implant to restrain the implant within the cannulus, and is further configured to couple with the implant to allow the implant to exit the distal end of the cannulus when the implant is pushed with a force small enough so as not to damage the function of the implant in the tissue;

wherein the channel of the implant extends all the way through the implant, wherein the restraining element has a distal end that extends past the distal end of the implant when the implant and pusher are so situated, but not past the distal end of the cannulus, and the distal end of the restraining element restrains the implant from sliding off the restraining element, and wherein a distal end of the restraining element is enlarged, but is configured so that the implant can slide off the distal end of the restraining element, when the implant is pushed with said force.

11. A device according to claim 10, wherein the implant is a soft tissue marker.

12. A device according to claim 10, wherein the implant comprises a helical coil.

13. A device according to claim 10, wherein the restraining element comprises a wire.

14. A device according to claim 10, wherein the restraining element restrains the implant by friction against a surface of the channel of the implant.

15. A device according to claim 10, wherein the function of the implant comprises folding on itself to define a volume with a smallest dimension greater than the diameter of the channel of the cannulus, when the implant is inserted into the tissue.

16. A device according to claim 10, wherein the restraining element is at least indirectly coupled to the cannulus, such that the restraining element does not move along the cannulus when the pusher pushes the implant through the distal end of the cannulus.

17. A device according to claim 10, also including a handle, wherein the cannulus and the restraining are anchored in the handle at their proximal ends.

18. A device according to claim 10, also including a handle adapted to be held by an operator with one hand when using the device to insert the implant in the tissue.

* * * * *

UNITED STATES PATENT AND TRADEMARK OFFICE
CERTIFICATE OF CORRECTION

| | | |
|---|---|---|
| PATENT NO. | : 7,942,843 B2 | Page 1 of 1 |
| APPLICATION NO. | : 12/503907 | |
| DATED | : May 17, 2011 | |
| INVENTOR(S) | : Michal Tune et al. | |

It is certified that error appears in the above-identified patent and that said Letters Patent is hereby corrected as shown below:

On the Title page, item 73 (assignee), insert -- , -- after "Ltd.".

Claim 1, col. 10, line 25, "distal and of" should read -- distal end of --.

Claim 8, col. 10, line 50, "cannulas" should read -- cannulus --.

Signed and Sealed this
Ninth Day of August, 2011

David J. Kappos
*Director of the United States Patent and Trademark Office*